(12) United States Patent
Beitz et al.

(10) Patent No.: US 7,314,582 B1
(45) Date of Patent: Jan. 1, 2008

(54) LANTHANIDE-HALIDE BASED HUMIDITY INDICATORS

(75) Inventors: James V. Beitz, Hinsdale, IL (US); Clayton W. Williams, Chicago, IL (US)

(73) Assignee: U.S. Department of Energy, Washington, DC (US)

( * ) Notice: Subject to any disclaimer, the term of this patent is extended or adjusted under 35 U.S.C. 154(b) by 539 days.

(21) Appl. No.: 10/839,203

(22) Filed: May 6, 2004

(51) Int. Cl.
*G01N 33/00* (2006.01)
*G01N 31/00* (2006.01)

(52) U.S. Cl. ................................ 252/408.1

(58) Field of Classification Search ............ 436/41, 436/39; 73/29.04; 423/466, 21.5
See application file for complete search history.

(56) References Cited

U.S. PATENT DOCUMENTS

| | | | | |
|---|---|---|---|---|
| 1,331,257 A | * | 2/1920 | Heap et al. | ........... 423/263 |
| 2,460,065 A | | 1/1949 | Davis | |
| 2,756,124 A | * | 7/1956 | Patterson et al. | ........... 423/257 |
| 2,777,856 A | * | 1/1957 | Stokes | ........... 548/303.4 |
| 3,646,080 A | * | 2/1972 | Pobiner | ........... 534/15 |
| 4,532,071 A | * | 7/1985 | Nakamura et al. | ... 252/301.4 H |
| 5,178,664 A | * | 1/1993 | Picard | ........... 75/300 |
| 5,607,619 A | * | 3/1997 | Dadgar et al. | ........... 252/187.2 |
| 6,043,096 A | | 3/2000 | Evtodienko et al. | |
| 6,066,305 A | * | 5/2000 | Dugger | ........... 423/263 |
| 6,753,184 B1 | * | 6/2004 | Moreton et al. | ........... 436/39 |
| 2005/0181119 A1 | * | 8/2005 | Tahon et al. | ........... 427/65 |

FOREIGN PATENT DOCUMENTS

WO    WO 02/057772    *    7/2002

OTHER PUBLICATIONS

Forsberg, J. H and Moeller, T. Observations on the Rare Earths. LXXIX. The Synhteses and Properties of Ethylenediamine Chelates of the Tripositive Lanthanide Ions Inorganic Chemistry, Vl. 8, No. 4, pp. 883-888, Apr. 1969.*
Greenwood, N. N. and Earnshaw, A. Chemistry of the Elements 1997, Butterworth Heinemann, Oxford, 2nd Ed. pp. 1227-1242.*
Tahon, et al., Method of Preparing Storage Phosphors from Dedicated Precursors, U.S. Appl. No. 60/535,971, filed Jan. 12, 2004.*

* cited by examiner

*Primary Examiner*—Gladys J P Corcoran
*Assistant Examiner*—Regina Yoo
(74) *Attorney, Agent, or Firm*—Brian J. Lally; Michael J. Dobbs; Paul A. Gottlieb

(57) ABSTRACT

The present invention discloses a lanthanide-halide based humidity indicator and method of producing such indicator. The color of the present invention indicates the humidity of an atmosphere to which it is exposed. For example, impregnating an adsorbent support such as silica gel with an aqueous solution of the europium-containing reagent solution described herein, and dehydrating the support to dryness forms a substance with a yellow color. When this substance is exposed to a humid atmosphere the water vapor from the air is adsorbed into the coating on the pore surface of the silica gel. As the water content of the coating increases, the visual color of the coated silica gel changes from yellow to white. The color change is due to the water combining with the lanthanide-halide complex on the pores of the gel.

21 Claims, 3 Drawing Sheets

LANTHANIDE-HALIDE BASED HUMIDITY INDICATORS

U.S. GOVERNMENT RIGHTS

The United States Government has rights in this invention pursuant to Contract No. W-31-109-ENG-38 between the U.S. Department of Energy and the University of Chicago, representing Argonne National Laboratory.

TECHNICAL FIELD

The present invention relates to a visual humidity indicator. Specifically, the invention relates to a reusable lanthanide-halide based humidity indicator that changes colors in the presence of minute amounts of water vapor.

BACKGROUND OF THE INVENTION

The maintenance of extremely low humidity environments is critical to a number of industries including: electronics manufacturing, (i.e. semi-conductors), pharmaceuticals, munitions storage, and specialty packaging. For example, the semi-conductor industry ships some of its products in extremely low humidity packaging (less than 5% relative humidity) to prevent corrosion. Even small amounts of humidity can corrode a semi-conductor, effect the quality of pharmaceuticals or destabilize munitions. A simple low-cost means for determining humidity levels is needed to monitor the integrity of such low humidity environments.

Humidity indicators range from simple visible indicators to complex electronic humidity devices. The most popular visible indicators employ cobalt salts (i.e. cobalt chloride) that change color when exposed to a certain level of relative humidity. See, for example U.S. Pat. Nos. 2,460,064 and 2,460,065 issued to Paul Bell Davis on Jan. 25, 1949. Cobalt salt indicators work well in moderate humidity levels but they are poor at indicating extremely low relative humidity levels (i.e. below 5%) at common ambient temperatures. Furthermore, in 2000 the European Union declared cobalt chloride, the most widely used humidity indicator salt, a class II carcinogen. This makes the use of cobalt chloride-based indicators undesirable.

Other types of visible indicators include devices that employ deliquescent chemicals or salts in combination with water soluble dyes. See, U.S. Pat. No. 2,249,867 issued to Snelling. Deliquescent indicators work in some situations, but their low heat resistance and tendency to undergo irreversible chemical change limit their potential use. Electronic humidity indicators have become more prevalent in recent years but they are not cost-effective for high volume applications.

In view of the prior art there is a need for a non-carcinogenic, cost-effective visual humidity indicator which can detect the presence of extremely low amounts of water vapor.

SUMMARY OF THE INVENTION

The present invention relates to a humidity indicator capable of detecting extremely low water vapor levels (<0.011% relative humidity at 295 K). The invented composition changes color when exposed to even small concentrations of water vapor, is capable of several hydration/dehydration cycles, and is both cost effective and easy to use.

A preferred embodiment undergoes a reversible color change from a solid yellow or red when fully dehydrated to a pale yellow-white when hydrated. See FIGS. 3A-D The color of the dehydrated form of the indicator can vary from yellow to a dark red (almost black). This variation in color is attributable to two factors. The indicator tends to be lighter (yellowish) when applied as a thin film and progressively gets darker (more red) as thickness is increased. Secondly, different hydrohalide mixtures tend to give slightly different colors.

The humidity indicator material is prepared using the following generalized steps:
1. Mixing an aqueous hydrohalide solution that contains dissolved free halogen with a lanthanide compound to form a lanthanide-halide solution;
2. (optional) Adding water to the lanthanide-halide solution;
3. (optional) Adding a dispersing agent to the lanthanide-halide (or lanthanide-halide-water) solution;
4. (optional) Allowing the lanthanide-halide solution to absorb into a porous, high surface area support;
5. Evaporating/Drying the solution and/support.

An advantage of the present invention is its ability to overcome the problems associated with prior art humidity indicators;

Another advantage of the present invention is its ability to detect very small amounts of water vapor.

Yet another advantage of the present invention is its ability to undergo multiple hydration/rehydration cycles at ambient temperatures while maintaining its ability to detect humidity levels.

Another advantage of the present invention is that it is non-carcinogenic;

Still another advantage of the present invention is its cost effectiveness for high volume applications.

Yet another advantage of the present invention is the speed in which it indicates a rise in humidity.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE PREFERRED EMBODIMENTS

Figure 1:
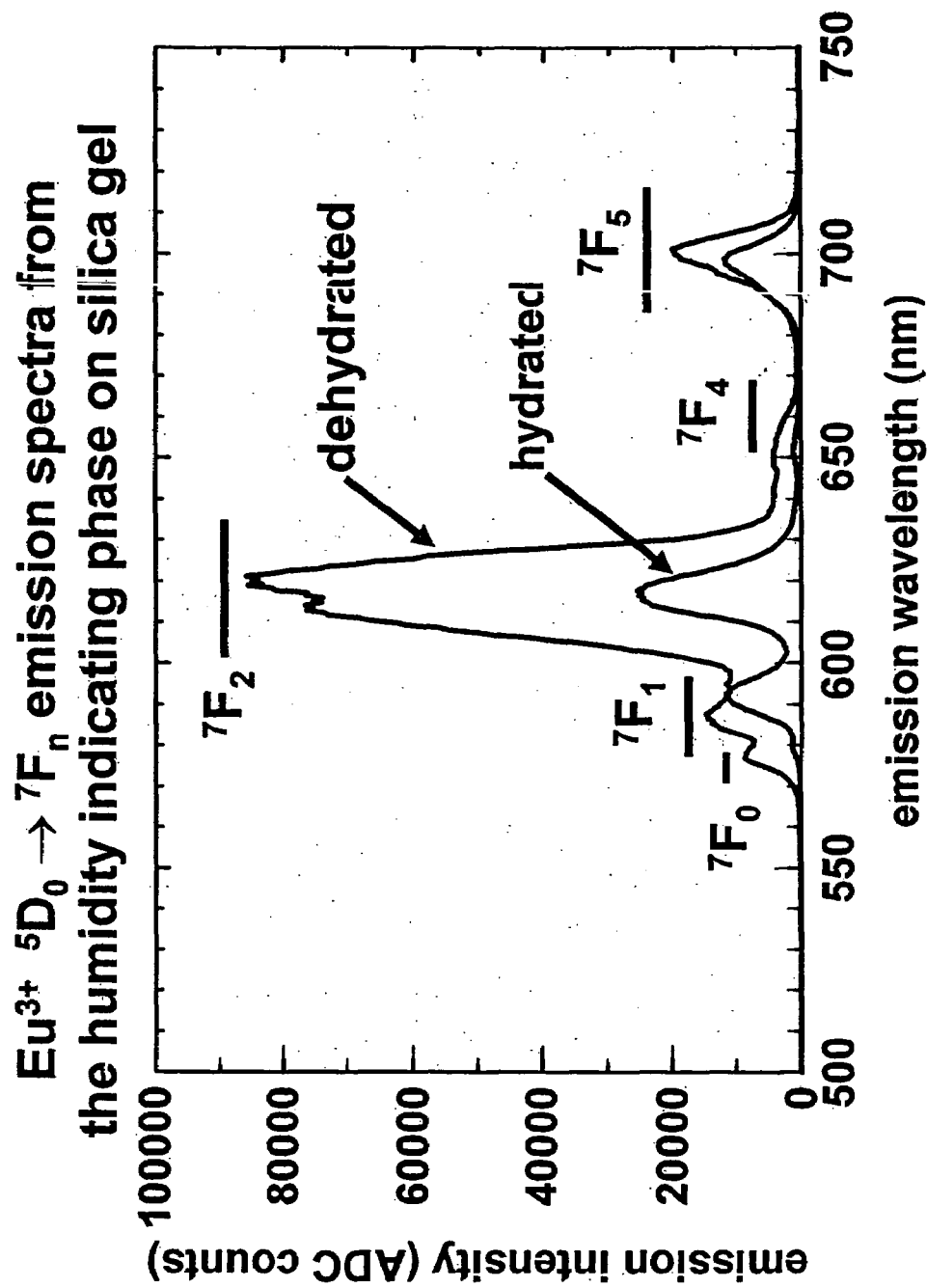
FIG. 1 illustrates $Eu^{3+}$ $^5D_0 \rightarrow {}^7F_n$ emission spectra at 500 nm to 750 nm from the humidity indicating phase on silica gel from a laser induced fluorescence study that used 355 nm excitation.

The present invention discloses a lanthanide-halide based humidity indicator and method of producing such indicator. The color of the present invention indicates the humidity of an atmosphere to which it is exposed. For example, impregnating an adsorbent support such as silica gel with an aqueous solution of the europium-containing reagent solution described herein, and dehydrating the support to dryness forms a substance with a yellow color. When this substance is exposed to a humid atmosphere the water vapor from the air is adsorbed into the coating on the pore surface of the silica gel. As the water content of the coating increases, the visual color of the coated silica gel changes from yellow to white. The color change is due to the water combining with the lanthanide-halide complex on the pores of the gel.

The basic unit of the present indicator complex is believed to be a trivalent lanthanide ion (i.e. $Eu^{3+}$) surrounded by six halide ions that are arranged to give a octahedral point of symmetry around the trivalent lanthanide ion. It is believed that the preferred embodiment of the indicator has the following general formula (s) in its dehydrated state, $AB_3.X.3CB$ (where A is lanthanide, B is a halogen ion, X is a (variable amount of) polyhalide ion, and C is a dispersing agent). The dehydrated complex forms when an aqueous solution that contains these ions and a hydrohalide is evaporated to dryness. The dehydrated complex contains trivalent lanthanide ions (i.e. $Eu^{3+}$), halide (i.e. $Br^-$) ions, polyhalide (i.e. $Br_3{-}$) ions, and a dispersing agent ion (i.e. $NH_4^+$). The complex is stable to at least 250° C. when heated under vacuum The present invention is ideally suited for several applications including the monitoring of humidity levels in extremely low humidity environments for packages. For example, a small sample of powder could be placed in a humidity free package to ensure its integrity. When the package is open the color of the indicator would immediately inform the recipient whether or not the package was compromised. The indicator could be similarly used for other humidity or very low humidity environments.

Method of Preparing Lanthanide-Based Humidity Indicators

The method of producing such indicator generally comprises the following steps:
a. Mixing an aqueous hydrohalide solution that contains dissolved free halogen with a lanthanide compound to form a lanthanide-halide solution;
(optional) Adding water to the lanthanide-halide solution forming a lanthanide-halide-water solution;
c. (optional) Adding a dispersing agent to the lanthanide-halide (or lanthanide-halide-water) solution;
d. (optional) Allowing the lanthanide-halide solution to absorb onto a porous, high surface support;
e. Evaporating off the liquid portion of the lanthanide-halide based solution or drying the high surface support.

Preparation of the Aqueous Hydrohalide Solution

The present invention requires an aqueous hydrohalide solution that is saturated or partially saturated with free halogen. Many stock hydrohalide solutions (i.e. HBr) contain no restrictions to the amount of free halogen present in solution. Therefore, it may be necessary to add free halogen (i.e. $Br_2$) to a stock hydrohalide solution. Several hydrohalide solutions are acceptable including but not limited to HBr, HCl and HI and mixtures of two more of the species HBr, HCl, and HI. The free halogen can be chlorine ($Cl_2$), bromine ($Br_2$) or iodine ($I_2$) or a mixture two or more the halogens $Cl_2$, $Br_2$ and $I_2$. The use of HBr that contains dissolved $Br_2$ is preferred.

If an aqueous solution of hydrobromic acid (HBr) is utilized, the amount of free halogen ($Br_2$) can be gauged by the optical density (OD) of the solution as pure HBr is a clear liquid while $Br_2$ has a much darker color. The presence (or addition) of free $Br_2$ in (to) aqueous HBr creates a darker solution. This color (or change in color) can be measured by optical absorbance to determine the amount of free halogen present in solution. The solution in a preferred embodiment had an optical density of approximately 0.90 absorbance units per centimeter of optical pathlength at 500 nanometers but it is believed that solutions with optical densities (OD) between 0.1 to 2.0 would also be acceptable, (at approximately 295 K). Solutions with ODs greater to or less than this range might also prove useful. A CARY model 17 dual beam spectrophotometer (Varian Inc., Palo Alto, Calif.) was used to measure OD in the present invention, although, other similar spectrophotometers could also be employed.

Spectrophotometric analysis is applicable to the hydrohalide solutions based on chlorine, bromine and iodine, either singly or in combination.

The hydrohalide solution containing sufficient amounts of free halogen can be prepared in advance and stored for short periods of time or it can be made directly before the subsequent steps. Storing prepared hydrohalide solutions for long periods of time (especially in the presence of light) is not recommended as some hydrohalide solutions have the tendency to disassociate. Alternatively, a hydrohalide having a specified free halogen content can be custom ordered.

Preparation of Lanthanide-Halide Solution

The prepared (or stored) hydrohalide solution (as described above) is combined with a lanthanide compound to form a lanthanide-halide solution. In a preferred embodiment europium sesequioxide ($Eu_2O_3$) is used but lanthanide metals, other lanthanide oxides and other lanthanide compounds are also acceptable. Other suitable lanthanide compounds include lanthanide trihalides (i.e. $EuBr_3$).

The hydrohalide solution and lanthanide compound are mixed at a HB:Ln molar ratio of between 3:1-75:1, preferably between 4:1-16:1, where HB is the hydrohalide acid and Ln is the lanthanide ion. The solution should be mixed until the lanthanide compound is completely dissolved in the solution.

In the absence of dissolved free halogen, evaporation of a dispersing agent-free lanthanide-halide solution creates solid lanthanide trihalide hexahydrate (i.e. $EuBr_3.6H_2O$) that is colorless and monoclinic. It is believed that the structure is composed of cationic complexes (i.e. $(Eu(H_2O)_6Br_2)^+$) and isolated halogen anions (i.e. $Br^-$), with the cations and anions occupying positions on $2^{nd}$ order symmetry axes. When the lanthanide-halide solution contains dissolved free halogen, some of the halogen anions are converted to polyhalide ions (i.e. $Br_3^-$). If the polyhalide ions primarily substitute for the isolated halogen anions in the structure, then the observed coloration can be understood as arising from enhanced charge transfer interaction between $Eu^{3+}$ ions and $Br_3^-$ due to closer proximity of $Eu^{3+}$ and $Br_3^-$ ions that results when intervening water molecules are lost during dehydration. Coloration is lost upon re-hydration that results in restoration of intervening water molecules due to increased separation of $Eu^{3+}$ and $Br_3^-$ and consequent reduction of the charge transfer interaction of those ions.

It is important that the lanthanide-halide solution has excess hydrohalide relative to the lanthanide to keep the solution acidic. The acidity of solution helps maintain the critical trivalent lanthanide ions (i.e. $Eu^{3+}$) and prevents the $Eu^{3+}$ ions from reacting with water and forming stable LnOB (i.e. EuOBr) compounds. (where Ln is a lanthanide and B is a halide).

Water can be added to the lanthanide-halide solution to decrease the volatility of the solution. The amount of water can added can be varied according to desired volatility levels as long as a pH of 4 or lower is maintained to prevent hydrolysis of the lanthanide ion(s).

The lanthanide-halide (or lanthanide-halide-water) solution can now be evaporated leaving a solid lanthanide-halide compound or the solution can be sorbed onto a high surface support and then dried.

Sorbing Halogen-Lanthanide Solution onto a High Volume Support

In a preferred embodiment the lanthanide-halide solution is sorbed onto a porous, high surface area support like silica gel. The high surface area support allows the application of a thin layer of halogen-lanthanide complex which improves (decreases) response time and reduces cost. Other suitable supports include but are not limited to $Al_2O_3$, $GeO_2$, $ZrO_2$ and $HfO_2$. The solution can be sorbed onto the support in a number of ways well known in the art. In the present embodiment the lanthanide-halide solution was added dropwise to a silica gel powder. A suitable range for the amount of solution to be sorbed onto the support is between 0.3 ml lanthanide-halide solution/1 g of support and 5 ml lanthanide-halide solution/1 g of support. Using more solution/g (support) is also likely to work but is less economical. The use of less than 0.1 ml/g might decrease the effectiveness of the final product.

An exemplary embodiment utilizes DAVISIL® brand silica gel (grade 645, 60-100 mesh powder, 1.15 ml/g nominal pore volume) manufactured by Grace of Columbia, Md. (formerly W.R. Grace Company). During drop-wise addition of the lanthanide-halide solution, the support is agitated by stirring to create a more uniform powder.

Drying Support or Evaporation of Solution

The final step of the present invention is to dry or evaporate the powder and or solution to dryness. The solution or powder can be dried (or evaporated) by many methods well known in the art including but not limited to: dry gas heat, dry gas flow, and vacuum heating. The method used will be determined by desired results. If time is at a premium vacuum heating is the fastest but also very expensive. The temperature should not exceed 523 K to avoid decomposition of the desired phase. Dry gas dehydration is the most economical but also the most time consuming. An exemplary method is to place the solution or gel powder under a nitrogen gas flow until it is evaporated/dehydrated.

In the preferred embodiment the powder should be dried until it becomes yellowish (or reddish) in color indicating that its dehydrated state.

The powder is now ready to be used as a humidity indicator. Due to the sensitivity of the material it is important that the humidity indicating material is kept in a humidity-free package if shipped in its dehydrated state. Alternatively, the material can be shipped in its hydrated state in regular packaging. The product can be re-dehydrated onsite where and when the material is going to be used.

Dispersing Agent

During development it was discovered that adding a dispersing agent to the lanthanide-halide solution increases the porosity of the end dehydrated product. The present embodiment utilized an ammonium-halide as the dispersing agent. If a halide containing dispersing agent is being used the halide should correspond to the halide(s) present in the humidity indicating material. For example, ammonium bromide can be used as a dispersing agent for lanthanide-bromide based humidity indicators.

While ammonium-halides are the preferred dispersing agents several other dispersing agents could also be employed including relatively large monovalent cations such as $K^+$, $Rb^+$, or $Cs^+$. The dispersing agent can be added to the solution at several junctures including after the addition of the lanthanide compound (or water if added). The dispersing agent is suitably added at a ratio of 1:1 or greater relative to the lanthanide in the solution.

RESULTS AND EXAMPLES

Figure 2:
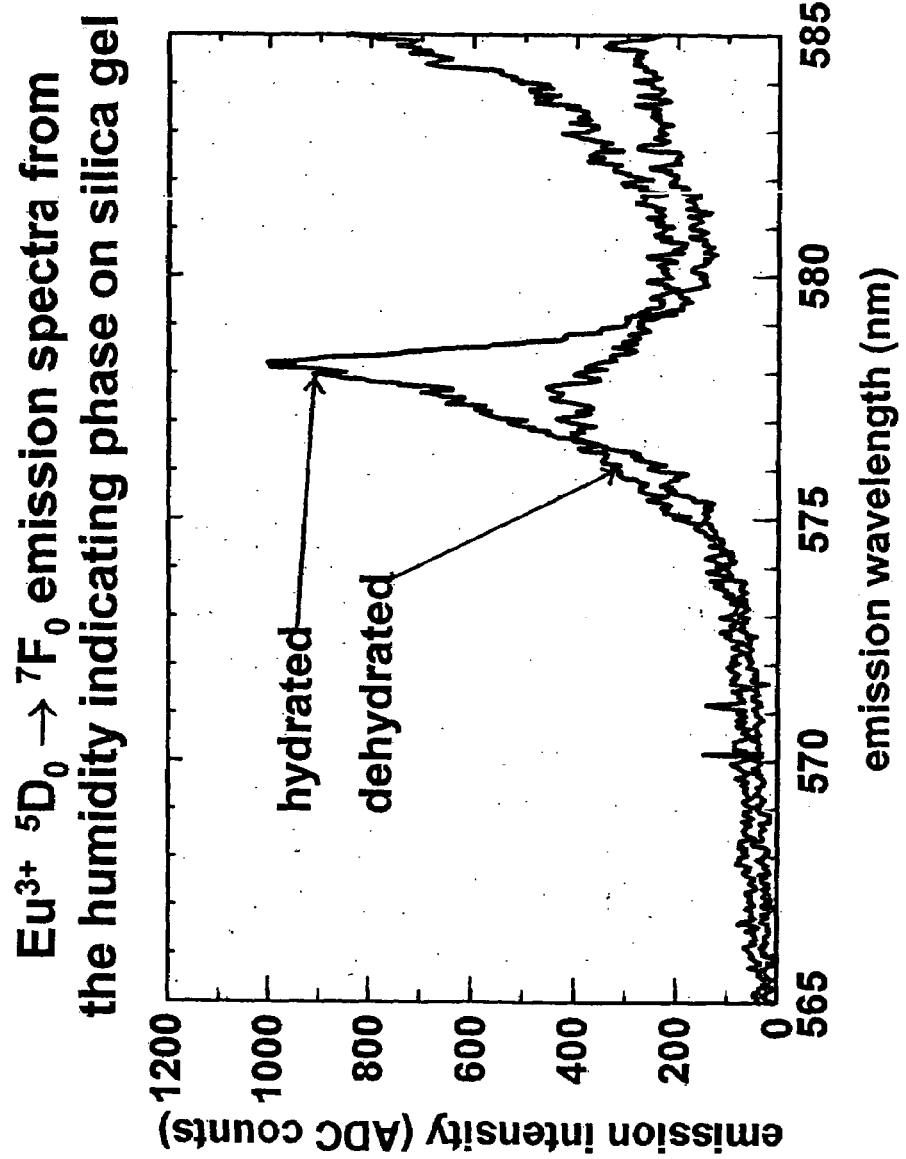
FIG. 2 illustrates $Eu^{3+}$ $^5D_0 \rightarrow {}^7F_0$ emission spectra at 565 nm to 585 nm from the humidity indicating phase on silica gel from a laser induced fluorescence study that used 355 nm excitation.
Figures 3A, 3B, 3C, 3D:
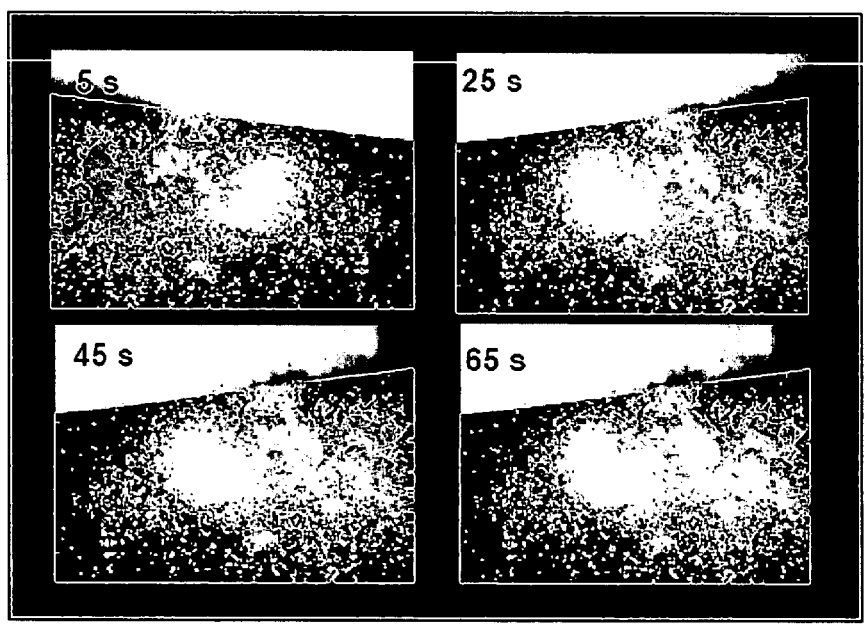
FIGS. 3A-D shows time lapsed photographs of a preferred embodiment of the invented indicator that were recorded as the indicator was exposed to still air having 58% relative humidity and a temperature of 296 K.

FIGS. 1 and 2 illustrate emission spectra from a preferred embodiment humidity indicating phase on silica gel from laser induced fluorescence studies. The decay rate, $K_{obs}$, ($s^{-1}$), of the $^5D_o$ state of $Eu^{3+}$ provides an estimate of inner sphere $H_2O$ molecules: $n=(K_{obs}-K_{nr})/1050$ where n is the number of inner sphere $H_2O$ molecules per $Eu^{3+}$ ion and $K_{nr}$ is the nonradiative decay rate of the $^5D_o$ state. Based on this relationship, there are (5.6±0.5) and (2.5±0.5) inner sphere coordinated $H_2O$ molecules in the hydrated and dehydrated phases, respectively. The number of $^5D_o$-$^7F_0$ bands identifies the number of $Eu^{3+}$ local environments. The intensity of the $^5D_o$-$^7F_0$ band vs. the $^5D_o$-$^7F_2$ is indicative of the degree of interaction of $Eu^{3+}$ ions with polarizable ligands such as $Br_3^-$ ions.

Dehydration results in a large increase in the intensity of the $^5D_o$-$^7F_2$ band relative to the $^5D_o$-$^7F_0$ band. This is evidence of increased interaction with a polarizable ligand. The increase principally is ascribed to enhanced interaction of $Eu^{3+}$ ions with surrounding $Br_3^-$ ions due to diminished distance between $Eu^{3+}$ and $Br_3^-$ ions upon dehydration. The observed single, symmetric $^5D_o$-$^7F_0$ band is consistent with the presence of a single type of local environment for $Eu^{3+}$ ions in the dehydrated phase. The structure of the $^5D_o$-$^7F_0$ band upon hydration is evidence that at least two $Eu^{3+}$ local environments are present and is consistent with hydration resulting in diminished interaction of $Eu^{3+}$ and $Br_3^-$ ions.

FIGS. 3A-D are time lapsed photographs of the invented indicator as it is exposed to still air having 58% relative humidity and a temperature of 296 K. These photographs clearly illustrate the invention's ability to quickly indicate the presence of humidity. There is a noticeable color change within the first 20 seconds and a dramatic color change over a 60 second interval.

A preferred embodiment of the present invention is described below:

Example 1

An aqueous hydrobromic acid solution (HBr) (containing dissolved free bromine) was formed by mixing liquid bromine ($Br_2$) with aqueous hydrobromic acid (~48% hydrogen bromide by weight) in an amount sufficient to from a solution with an optical density of 0.90 per cm of optical pathlength at 500 nanometers. 3.34 g of the prepared hydrobromic acid-free bromine solution was mixed with 0.28 g of europium sesquioxide ($Eu_2O_3$) and the solution was mixed until the $Eu_2O_3$ was dissolved forming a europium-bromide mixture. 2.40 g of water was added to the europium-bromide mixture forming a europium-bromide-water solution. 1.10 g of ammonium bromide ($NH_4Br$) was mixed with the europium-bromide-water mixture to give a humidity indicating solution. 1.15 ml of the humidity indicating solution was added dropwise to 1.00 g of porous, high surface area silica gel. The sorbed silica gel was then dried under nitrogen gas flow until it turned yellow indicating its anhydrous state.

The present invention is most useful when used in a temperature range of 0-140° C., more preferably between 15-40° C.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. Accordingly, the invention is limited only by the following claims and equivalents thereto.

The embodiment of the invention in which an exclusive property or privilege is claimed is defined as follows:

1. Method of producing a lanthanide-halide based humidity indicator comprising:
   a. preparing an aqueous hydrohalide solution at least partially saturated with a free halogen;
   b. mixing said aqueous hydrohalide solution with lanthanide containing compound forming an acidic lanthanide-halide solution;
   c. evaporating the lanthanide-halide solution until it changes color forming a lanthanide-halide based humidity indicator;
   d. said evaporated lanthanide-halide based humidity indicator has the formula of $AB_3 \cdot X \cdot 3CB$ whereas A is a lanthanide; B is a halogen ion; X is one or more polyhalide ions; and C is a dispersing agent;
   e. whereby said aqueous hydrohalide is comprised of aqueous HBr and said step of preparing an aqueous hydrohalide solution comprises adding free halogen in a sufficient amount to said aqueous hydrohalide solution whereby said hydrohalide solution has an optical density between 0.1-2.0 per cm of pathlength at 500 nm;
   f. said lanthanide-halide solution has a pH of four or lower; and
      further comprising the step of mixing water into the lanthanide-halide solution while maintaining said pH of said lanthanide-halide solution at four or lower.

2. The method described in claim 1, further comprising: mixing a dispersing agent into the lanthanide-halide solution wherein the molar ratio of dispersing agent to lanthanide is 1:1 or greater.

3. The method described in claim 2, wherein the dispersing agent is a halide salt of cations selected from the group consisting of: $NH_4^+$, $K^+$, $Rb^+$, $Cs^+$ and combinations thereof.

4. The Method of producing a lanthanide-halide based humidity indicator of claim 2, wherein the dispersing agent is a halide salt of cations selected from the group consisting of: $K^+$, $Rb^+$, $Cs^+$.

5. The method described in claim 1, wherein said aqueous hydrohalide solution is prepared by adding free halogen in a sufficient amount to said aqueous hydrohalide solution whereby the hydrohalide solution has an optical density of approximately 0.9 per cm of pathlength at 500 nm.

6. The method described in claim 1, wherein the hydrohalide solution is saturated with dissolved free halogen selected from the group consisting of $Cl_2$, $Br_2$, $I_2$ and combinations thereof.

7. The method described in claim 1, wherein the hydrohalide solution is partially saturated with dissolved free halogen selected from the group consisting of $Cl_2$, $Br_2$, $I_2$ and combinations thereof.

8. The method described in claim 1, wherein the lanthanide in the lanthanide-containing compound is europium (Eu), samarium (Sm), thulium (Tm), ytterbium (Yb) or combinations thereof.

9. The method described in claim 1, wherein the lanthanide containing compound is $Eu_2O_3$.

10. The method described in claim 1, wherein the lanthanide containing compound is a lanthanide oxide, oxyhydroxide, trihydroxide, lanthanide oxyhalide, lanthanide metal.

11. The method described in claim 1, wherein the lanthanide containing compound is a lanthanide tri-halogen.

12. The method described in claim 1, wherein the lanthanide-halide solution is evaporated by heating, using temperatures not exceeding 523 K.

13. The method described in claim 1, wherein the lanthanide-halide solution is evaporated by dry gas dehydration.

14. The method described in claim 1 wherein the ratio between the hydro-halide and lanthanide ions is between 3:1 and 75:1 in the lanthanide-halide solution.

15. The method described in claim 1, wherein the hydrohalide and lanthanide containing compound are mixed in a molar ratio of between 5:1 and 150:1.

16. The method described in claim 1 further comprising:
   a step of sorbing the lanthanide-halide solution onto a porous support, prior to evaporation, forming a sorbed-support.

17. The method as described in claim 16 wherein the porous support is selected from the group consisting of silica gel, $Al_2O_3$, $GeO_2$, $HfO_2$ and $ZrO_2$.

18. The method as described in claim 16, wherein the porous support is silica gel or silica powder.

19. The method as described in claim 16, wherein the amount of lanthanide-halide solution sorbed onto the support is between 0.3 ml solution/1 g support and 5 ml solution/1 g support.

20. The method described in claim 1, including the step of evaporating said lanthanide-halide solution until said lanthanide-halide solution has a yellow or dark red color; and
   wherein the hydrohalide solution is comprised of aqueous HBr containing dissolved free bromine and the lanthanide containing compound is $Eu_2O_3$.

21. The method described in claim 20, further comprising the step of packaging said lanthanide-halide based humidity indicator in a humidity-free package.

* * * * *